United States Patent [19]

Shoberg

[11] 4,077,515
[45] Mar. 7, 1978

[54] MEDICAL SLIDE CASE WITH HINGED MOLDED SECTIONS

[76] Inventor: Dell Shoberg, 18748-2 Bryant St., Northridge, Calif. 91324

[21] Appl. No.: 730,124

[22] Filed: Oct. 6, 1976

[51] Int. Cl.² ............................................. B65D 85/48
[52] U.S. Cl. .................................. 206/456; 220/4 E; 220/339
[58] Field of Search ............... 220/4 B, 4 E, 339; 206/456, 454, 455, 564, 565, 587

[56] References Cited

U.S. PATENT DOCUMENTS

| 2,197,859 | 4/1940 | Freed | 206/456 |
|---|---|---|---|
| 2,984,341 | 5/1961 | Homburger | 206/456 |
| 3,037,616 | 6/1962 | Phipps | 220/339 X |
| 3,251,460 | 5/1966 | Edmonds | 220/4 E X |
| 3,344,913 | 10/1967 | Best | 220/339 X |
| 3,410,391 | 11/1968 | Kanter | 220/339 X |
| 3,511,433 | 5/1970 | Andrews et al. | 220/339 X |
| 3,551,940 | 1/1971 | Edison | 220/339 X |
| 3,557,489 | 1/1971 | Ferrand | 220/4 E X |
| 3,746,161 | 7/1973 | Jones | 206/456 |
| 3,825,112 | 7/1974 | Schumaker | 220/339 X |

FOREIGN PATENT DOCUMENTS

| 557,208 | 2/1957 | Italy | 220/339 |
|---|---|---|---|
| 1,127,611 | 9/1968 | United Kingdom | 220/4 E |

Primary Examiner—Robert S. Ward, Jr.
Attorney, Agent, or Firm—Neil J. Driscoll

[57] ABSTRACT

A medical slide enclosure case comprises non-separable congruently mirrored segments of molded plastic. The segments are joined by an integrally molded thin hinge line. Case closure is accomplished by molded hooks on the segments in snap closure alignment with molded wall edges and opposed to the hinge line. Case segments include internal walls defining a slide receiving cavity. The cavity includes spacer ledges to maintain the received slide surfaces in spaced relation to the inner case surfaces. The case includes a defined finger cavity adjacent to slide cavity facilitating easy insert and removal of the medical slide from the case.

3 Claims, 6 Drawing Figures

U.S. Patent     March 7, 1978     4,077,515
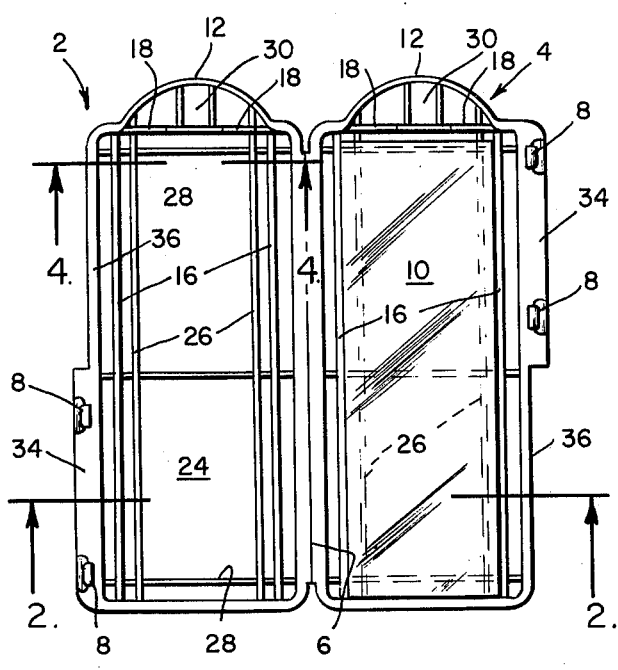
Fig. 1.
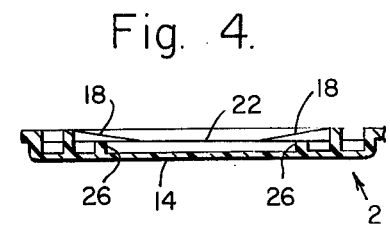
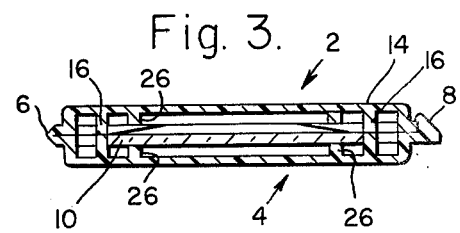
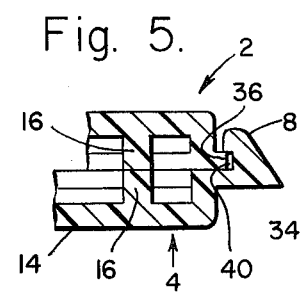
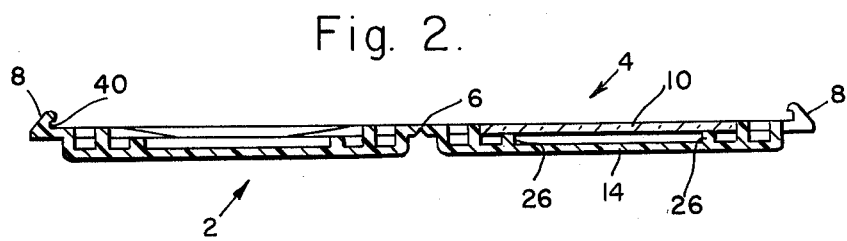
Fig. 2.
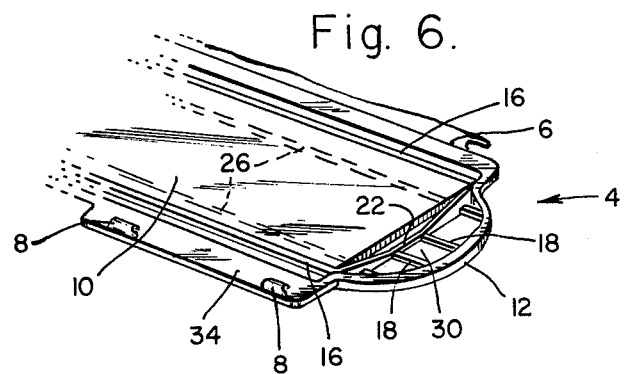
Fig. 6.

MEDICAL SLIDE CASE WITH HINGED MOLDED SECTIONS

The invention relates to a medical slide case having structural features to facilitate the storage and transport of medical slides while preserving the slides in an uncontaminated and undamaged condition.

Laboratory analysis of bodily fluids, tissue for bodily excretions is a frequently used tool of modern medical practice. Usually the body sample is obtained by the doctor in an appropriate examining location, such as his office or the examining room of a hospital. Characteristically, the sample obtained from the patient is placed on a cleaned or sterilized clear glass medical slide at the examination situs. The slide is then sprayed or coated with a solution of clear wax and isopropyl alcohol which assures adherence of the bodily sample to the slide. The medical personnel handling the slide must be extremely careful to maintain the slide clean, free of finger prints or other contaminants and in some cases maintain the slide in a sterile condition prior to receiving the bodily sample or smear. Frequently, many slides are obtained during the normal working period at a patient examining location. After the slide is obtained, it must be stored, marked, and transported to a central laboratory for appropriate medical analysis of the slide containing tissue or smear. During storage and transport to the medical lab, the slide is placed in an enclosure case and, all too frequently, with prior art cases, the slide arrives at the medical laboratory in a contaminated or damaged condition, frequently necessitating that the sample be retaken so that proper medical analysis can be achieved.

Accordingly, it is a primary object of the invention to provide a medical slide case to accommodate the storage and transport of a medical slide from the patient examining situs to the laboratory situs in an improved and facile manner.

It is a further object of the invention to provide a medical slide case having structural features designed to avoid abrasive, contaminating contact with the slide surfaces during storage and/or transport to the medical laboratory.

It is yet another object of the invention to provide a medical slide case having structural features to facilitate finger manipulation during the insertion and removal of the slide from the case to avoid accidental slide surface contamination.

It is yet another object of the invention to provide a medical slide case having the structural features described in combination with a closure arrangement which maintains each slide case in a firmly closed and flat condition during storage and transport thereof and facilitates opening and closing in a manner to minimize accidental damage.

These and other novel features and objects of the invention become apparent in the course of the following description and from an examination of the related drawings, wherein:

FIG. 1 is a plan view of the congruently mirrored non-separable halves of the slide case;

FIG. 2 is a sectional view taken along line 2—2 of FIG. 1 and showing the slide case in open position;

FIG. 3 is a transverse, central sectional view of the case and showing the case in closed condition;

FIG. 4 is a sectional view taken along line 4—4 of FIG. 1 showing some structural details of the finger cavity used in the invention;

FIG. 5 is a fragmentary sectional detail view of the case closure hook used in the invention; and, FIG. 6 is a perspective view showing finger removal of the slide from the case.

Slide cases in prior art arrangements have frequently been made of cardboard, pressed paper or the like. With increased use of laboratory analyses as a diagnostic medical technique, the disadvantages of such medical slide cases have become more apparent. For example, surfaces of the contained slide were frequently abraded by contact with the case surfaces which increased the difficulty of proper laboratory analysis. Many prior art cases were moisture-absorbent and, in certain atmospheres, resulted in container swelling and consequent damage to the contained slide. Further, while prior art cases were economical in first cost, they would not withstand the handling and abuse incident to frequent use, storage and transport and, consequently, had minimal service life.

The disclosed medical slide case incorporates, in its preferred embodiment, a molded plastic case preferably polypropylene construction. This material is lint-free, highly inert, non-hygroscopic, smooth-surfaced and, therefore, ideal for the service application described.

Directing attention to the FIGURES and particularly FIGS. 1, 2, and 3, it will be seen that the medical slide case comprises generally congruently mirrored left and right sections indicated generally at 2 and 4 respectively. The sections 2 and 4 are integrally joined at the adjacent edge by a thin hinge or pivot segment 6 which allows the section 2 to fold over and overlie to section 4 and accommodate case closure as is shown in FIG. 3. Hook clasps 8—8 maintain the sections 2 and 4 in closed condition as will be hereinafter described in detail. In the plan view of FIG. 1, a medical slide 10 is shown in position in the righthand section 4. Noting that the sections 2 and 4 are substantially of identical construction, a detailed description of the respective sections will be limited to the showing of section 2.

Section 2 comprises annular wall 12 which, together with bottom wall 14, defines a tub-like depression throughout the entire physical configuration of this section 2. Longitudinally delongated walls 16—16 are integrally formed to upstand from bottom wall 14 and have their upper edges coplaner with the upper edge of annular wall 12. A transverse end wall 18 is formed adjacent to the upper end of section 2 and has its opposed ends, 20—20, co-planar with the upper edge of walls 16 and is tapered downwardly toward a flat segment 22 centrally at section 2 (FIG. 4). It will thus be seen that the longitudinal walls 16, the lower segment of annular wall 12, and the tapered end wall of 18 define a slide receiving cavity 24.

Longitudinal spacer ledges 26,26 and transverse spacer ledges 28,28 are also integrally formed to upstand from the bottom wall 14 within the confines of slide cavity 24 and serve to support the received slide 10 and maintain the major portion of the surface thereof in spaced relation from the inner surface of the bottom wall 14 and thereby prevent slide surface contamination or destruction due to abrasive contact with the surfaces of the encapsulating case. The upper edges, as seen in FIG. 2, of spacer ledges 26 and 28 are, of course, coplaner.

End wall 18 and the adjacent segment of annular wall 12 define a second finger cavity receiving cavity 30 in longitudinal edge relation to the slide cavity 24. Recalling that end wall 8 is tapered downwardly to a central flat segment 22 (FIG. 4) it will be understood that the segment 22 is lower than the co-planar upper edges of spacer ledges 26 and 28 (FIG. 4). It will be apparent that a finger placed in cavity 30 can easily engage the end of slide 10 and thus facilitate the careful removal of the slide 10 from the case without accidental damage or contamination to the surface of the slide 10 (see FIG. 6).

It will also be understood that the annular wall 12, the longitudinal wall 16,16, the end wall 18 and the spacer ledges 26 and 28 serve as reinforcing webs to maintain the physical integrity and flatness of the medical case even after long service use.

Referring specifically to the FIGS. 1 and 5, it will be seen that each section 2 and 4 is provided with an outwardly directed integrally formed web 34,34. The webs 34 are identical in construction and, though not congruently mirrored, are each in operative alignment with a thin wall element 36,36 formed on the opposing section. Each web 34 has a pair of upwardly projecting hook clasps 8 integrally formed therein and as earlier referred to. The hook portion 38 of each clasp 8 defines a locking gap 40 adapted for the snap reception of the element 36 upon case closure as is shown in FIG. 5. It will be understood that each clasp 8 will bias rotatively outwardly as shown in FIG. 5 to accommodate the locking reception of element 36, and will spring back into locking engagement when that reception is complete. It will be noted that web 34 of section 2 is formed over the entire lower half of said section while the element 34 on section 4 is formed over the entire upper half on this respective section. It will also be noted that the hook clasps 8 are uniformly spaced longitudinally in the case in respective sections 34. It also will be understood that the clasps 8 maintain the entire longitudinal length of the medical case in proper closed condition during storage and transport, avoiding the entrance of foreign matter therein and additionally maintaining the entire case in a flat condition when closed and easy storage. Further, webs 34, due to the fact they project outwardly from the annular wall 12 on the upper and lower halves of the respective section, provide an easy mode for opening the case and that the fingers may be placed along the hinge 6 with the thumbs arranged in easy engaging relationship to the webs 34 to rotatively bias the webs and thereby open the case. The ease of opening and closing the case, as above described, substantially contributes to ease of handling of the medical slide with minimum slide damage.

It will also be understood that the preferred embodiment described above may be expanded to unitary medical slide cases adapted to hold two or more slides.

Functionally summarizing the above, it will be understood by those familiar with this art that a medical slide case is provided which substantially improves the efficiency and reliability of the handling and transport of medical slides and the same is accomplished in an economical and facile manner.

The invention as above described is without limitation and may be subject to further modification, all within the scope of the appended Claims.

What is claimed is:

1. In a case for the storage and transport of medical slides, generally planar sections of molded material integrally joined along one edge aspect of the respective sections, said juncture comprising a thin linear hinge element accommodating reversible movement of the sections from a planar case open condition to a planar case closed flat condition of the sections to thereby encapsulate a contained medical slide, each section comprising annular wall means having a planar upper edge generally defining a slide receiving cavity in each section, the cavities in each section being in congruent mirrored relation and adapted to receive said slide when the sections are in case open condition, the upper edges of the respective wall means on the respective sections being in close facing relation with each other when the sections are in closed condition, said wall means on at least one of said sections defining a second cavity adjacent said slide receiving cavity, said wall means having an interruption in the area of adjacency between the slide receiving cavity and the second cavity to accomodate finger insertion and edge engagement with a case received slide facilitating insertion and removal thereof, clasp means on the respective sections to maintain said sections in closed relation to each other, said clasp means comprising a web on each section formed in the plane of the section and extending outwardly from the annular wall means along an edge aspect thereof opposite the hinge element, each web on each section including an enlarged outward projection adapted for thumb engagement by the user for the application of rotative force on each section and about the hinge element to accomodate easy opening of the case, and flexible hook means carried by the web on each section for locking cooperation with a segment of the web on the other section.

2. A case for the storage and transport of medical slides according to claim 1, and including ledges in the slide receiving cavity in each section to maintain the surface of the received slide in spaced relation to the adjacent cavity surface of the respective sections, said annular wall means on each section including first slide embracing walls extending generally parallel to the linear hinge element and a second wall extending generally perpendicular to said linear hinge element, said second wall being adapted to separate the slide receiving cavity and the second cavity, said second wall being tapered as seen in elevational view to accomodate finger edge engagement with a case received slide.

3. A case for the storage and transport of medical slides according to claim 2, wherein the enlarged outward projection on each web of each section carries a plurality of flexible hook means for locking cooperation with an aligned segment of the web on the other section to provide spaced case locks over the length of the hinge element.

* * * * *